United States Patent [19]
Wintermeyer et al.

[11] Patent Number: 4,727,147
[45] Date of Patent: Feb. 23, 1988

[54] OPTICALLY ACTIVE 1-(4-METHOXYBENZYL)-1,2,3,4,5,6,7,8-OCTAHYDROISOQUINOLINIUM ACETATES

[75] Inventors: Willi Wintermeyer, Seeheim-Jugenheim; Fritz Reiff, Seeheim, both of Fed. Rep. of Germany; Hans R. Müller; Josef Conti, both of Schaffhausen, Switzerland

[73] Assignee: Merck Patent Gesellschaft mit beschrankter Haftung, Darmstadt, Fed. Rep. of Germany

[21] Appl. No.: 783,518

[22] Filed: Oct. 3, 1985

[30] Foreign Application Priority Data

Oct. 3, 1984 [DE] Fed. Rep. of Germany ....... 3436179

[51] Int. Cl.$^4$ ............................................. C07D 217/16
[52] U.S. Cl. ................................................ 546/149
[58] Field of Search ......................................... 546/149

[56] References Cited

FOREIGN PATENT DOCUMENTS 2003486 8/1970 Fed. Rep. of Germany .

OTHER PUBLICATIONS

Quart, Rev. 25 (1971) 323 Methods of Optical Resolution 323–341, Hydroxy-Morphinane VI 56 pp. 1376–1387, A. Brossi and O. Schnider.
Fr. Chem. Soc. Bull. 1972, p. 127 (pp. 1–40) Andre Collet et al.
Study of Mixtures of Optical Antipodes, pp. 2–9, Andre Collet et al.
Chemical Reviews, Jun. 1980, vol. 80, No. 3, pp. 216–230.
Onda, et al., "Chemical Abstracts", vol. 80, 1974, col. 47877h.
Morton, *Laboratory Technique in Organic Chemistry*, 1938, McGraw Hill, N.Y. p. 154.

Primary Examiner—Glennon H. Hollrah
Assistant Examiner—James H. Turnipseed
Attorney, Agent, or Firm—Millen & White

[57] ABSTRACT

Racemic 1-(4-methoxybenzyl)-1,2,3,4,5,6,7,8-octahydroisoquinoline can be resolved by seeding the supersaturated solution of racemic 1-(4-methoxybenzyl)-octahydroisoquinolinium acetate with its enantiomeric forms and crystallizing the optically active acetate corresponding to the configuration of the seed crystals. The continuous form of the process permits obtaining the two enantiomers together.

4 Claims, No Drawings

OPTICALLY ACTIVE 1-(4-METHOXYBENZYL)-1,2,3,4,5,6,7,8-OCTAHYDROISOQUINOLINIUM ACETATES

BACKGROUND OF THE INVENTION

The invention relates to a process for preparing optically active 1-(4-methoxybenzyl)-1,2,3,4,5,6,7,8-octahydroisoquinoline.

Optically active enantiomers of methoxybenzyloctahydroisoquinoline are useful intermediates for preparing pharmacologically active compounds such as optically active 3-methoxy-17-methylmorphinans which find utility as antitussives and analgesics.

Separation of enantiomers at an early stage of morphinan synthesis and if desired the return of the undesired isomer is of great importance to the economics of the process of preparation.

There are already various known processes for the optical resolution of (R,S)-1-(4-methoxybenzyl)-octahydroisoquinoline. Brossi and Schnider, Helv. Chim. Acta 39 (1965) 1376–86, described the separation by means of fractional crystallisation of the diastereoisomeric D-(−)-mandelic acid salts. German Pat. No. 2,003,486 discloses the separation into the antipodes by means of optically active (−)-di-O-isopropylidine-2-keto-L-gulonic acid.

These processes have the disadvantage that their implementation requires a costly optically active resolution reagent which is only available in one enantiomeric form and, after the optical resolution has been effected, is only incompletely regenerable again.

SUMMARY OF THE INVENTION

It is thus an object of this invention to provide a resolution process which permits the simple and complete isolation of the two enantiomers without the use of an optically active auxiliary reagent.

Upon further study of the specification and appended claims, further objects and advantages of this invention will become apparent to those skilled in the art.

These objects have been ahcieved by means of the process according to the invention for preparing optically active 1-(4-methoxybenzyl)-octahydroisoquinoline through spontaneous crystallization of the corresponding acetates.

The invention accordingly provides a process for preparing optically active 1-(4-methoxybenzyl)-1,2,3,4,5,6,7,8-octahydroisoquinoline, characterised in that a supersaturated solution of racemic 1-(4-methoxybenzyl)-octahydroisoquinolinium acetate is seeded with one of its enantiomeric forms and the optically active acetate which corresponds to the configuration of the seed crystals is crystallized.

The invention further provides the continuous variant of the process according to the invention for the purpose of obtaining the two enantiomers together.

The invention also provides (R,S)-1-(4-methoxybenzyl)-1,2,3,4,5,6,7,8-octahydroisoquinolinium acetate, (R)-1-(4-methoxybenzyl)-1,2,3,4,5,6,7,8-octahydroisoquinolinium acetate and (S)-1-(4-methoxybenzyl)-1,2,3,4,5,6,7,8-octahydroisoquinolinium acetate.

DETAILED DISCUSSION

Of the customary methods of resolving racemates of optically active amines (reviewed in: P. H. Boyle, Quart. Rev. 25 (1971) 323–341), such as, for example, diastereoisomerization with an optically active auxiliary reagent and their separation; chromatography on optically active phases; or asymmetrical decomposition by biological or chemical methods, spontaneous crystallization of an enantiomer or one of its derivatives is a relatively rarely used method [see Collet et al.: Optical Resolution by Direct Crystallization of Enantiomer Mixtures; Chem. Rev. 80 (1980) 215–38].

Preconditions for direct crystallisation of an enantiomer from its racemate include (a) the crystallization of the racemate as a conglomerate (b) a lower solubility of the enantiomers in question than that of the racemate form, and (c) crystallization of the respective enantiomer without delay.

A priori it is not possible to say in advance whether a racemate will crystallize as a conglomerate and hence will be accessible to resolution by spontaneous crystallization. The known examples (inter alia Collet et al., Bull. Soc. Chem. Fr. 1972 127; id. ibid. 1977 494) include in the main aminocarboxylic acids, while the number of pure amines is very small.

It was therefore all the more surprising that in the acetate of (R,S)-1-(4-methoxybenzyl)-octahydroisoquinoline it has been possible to find a salt which can be optically resolved by spontaneous crystallization.

The 1-(4-methoxybenzyl)-octahydroisoquinolinium acetate required for carrying out the process according to the invention can be easily obtained from the components in conventional manner. A particularly advantageous method is the preparation in situ by combining equimolar amounts of 1-(4-methoxybenzyl)-octahydroisoquinoline and glacial acetic acid in a solvent suitable for carrying out the spontaneous crystallization.

Suitable solvents are water, alkanols having 1 to 6C atoms, alkanones having 3 to 6C atoms or mixtures of these solvents. Preferred solvents are alcohols, in particular isopropanol.

Supersaturated solutions of racemic 1-(4-methoxybenzyl)-octahydroisoquinolinium acetate can be obtained in conventional manner using known methods, for example by concentrating (evaporating the solvent) or by adding a further solvent. The best method is to cool down a hot-saturated solution of the acetate and, owing to the lower solubility at lower temperature, in this way convert the solution into the supersaturated state. To prepare the supersaturated solution it is not necessary to use a 1:1 mixture of the enantiomers; on the contrary, it is of advantage to have one antipode present in excess and to allow this antipode to crystallize out spontaneously on cooling down. The saturated solution can be prepared at temperatures of 50°–150° C.

A supersaturated solution of racemic 1-(4-methoxybenzyl)-octahydroisoquinolinium acetate is treated in the process according to the invention with a small amount of a crystalline enantiomer (seeding). This can be effected in such a way that this quantity is dissolved in the hot supersaturated solution of the racemate and allowed to cool down and in this way the added enantiomer is allowed to crystallize out spontaneously; or the already cold super-saturated solution has added to it a small amount of optically uniform seed crystals or a portion of the seed crystals is dissolved by heating and the remainder is added after cooling down to the crystallization temperature. Stirring generally facilitates the crystallization.

The temperature range in which the crystallization is carried out is preferably 0° to 50° C., in particular at around 0° C.

An adequate amount of seed crystals to be added to the supersaturated solution is 0.05 to 5%, preferably 0.5 to 5%, relative to the weight of the solution. The seed crystals should be of high optical purity in order to avoid any possible concomitant crystallization of the unwanted isomer. After crystallization and isolation by, for example, filtration or centrifuging of one of the enantiomers, the mother liquor is left with an excess of the other enantiomer.

In a further preferred embodiment of the invention, this other enantiomer can be obtained by converting the mother liquor again into a solution which is supersaturated with respect to the racemate. This conversion can be accomplished either by concentrating the mother liquor, i.e. by evaporating the solvent, or by adding a certain amount of racemic 1-(4-methoxybenzyl)-octahydroisoquinolinium acetate. It is preferable to add that amount of racemate which corresponds to the amount of enantiomer separated off, the addition occurring, e.g., in the elevated temperature range mentioned above.

The spontaneous crystallization can be carried out in the same way as described above, with the exception that in this instance the seeding is with crystals of the antipode of the previously crystallized enantiomer. This procedure is preferably repeated a plurality of times with successive and alternate separation off of the optically active enantiomers and addition of racemic compound.

In this way it is possible to resolve racemic (R,S)-1-(4-methoxybenzyl)-octahydroisoquinolinium acetate completely into the enantiomers in a simple manner.

According to the invention, the isolated optically active 1-(4-methoxybenzyl)-octahydroisoquinolinium acetate can easily be made to yield the free amines.

The optically active (R)- or (S)-acetate crystals obtained, for example, by filtration or centrifuging are freed by treatment with an inorganic base. Suitable bases are all bases customarily used for this purpose, for example alkali metal and alkaline earth metal hydroxides, carbonates and hydrogen carbonates and also ammonia, strong organic bases and basic ion exchangers. Preferred bases are alkali metal hydroxides and ammonia, in particular potassium hydroxide and sodium hydroxide. The freeing of the optically active 1-(4-methoxybenzyl)-octahydroisoquinoline is effected by addition of a base to a solution of the optically active acetate in a suitable solvent, preferably water. By means of an organic solvent, such as, for example, diethyl ether, toluene, ethyl acetate, dichloromethane or mixtures thereof, it is then possible to extract the freed amine. If necessary after washing the extract the solvent is removed and in this way the desired optically active amine is obtained.

In performing the repetitive process of fractional crystallizing the two enantiomers preferably 20-60% of a given enantiomer are crystallized during one separation step. With respect to optical purity the relative percentage of enantiomer recovered is not critical.

The time range during which the crystallization is carried out is preferably 1-10 hours, in particular 1-5 hours.

Supersaturated solutions required for carrying out the separation process according to the invention preferably contain 1.1-3 times the fully saturated amount.

The present invention thus makes available a very advantageous process for optically resolving (R,S)-1-(4-methoxybenzyl)-octahydroisoquinoline simply, completely and in high yield without use of a chiral auxiliary reagent.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A solution of 300 g of racemic 1-(4-methoxybenzyl)-octahydroisoquinoline in 300 ml of isopropanol has added to it 67 ml of glacial acetic acid and, after cooling down to 0° C., is seeded with (S)-1-(4-methoxybenzyl)-octahydroisoquinolinium acetate. The result is a thick crystalline mass which is filtered off and washed with diethyl ether. This gives 56.5 g (30.5% of theory) of (S)-acetate; melting point: 89.5° C.; $[\alpha]_D^{20} = -118.7°$ C. (c=2% in methanol).

The seed material is obtained from pure (S)-1-(4-methoxybenzyl)-octahydroisoquinoline (3 g) in 8 ml of tert.-butyl methyl ether by addition of glacial acetic acid (0.67 ml). Yield: 3.49 g (94.3% of theory); melting point: 90° C., $[\alpha]_D^{20} = -119°$ (c=2% in methanol).

EXAMPLE 2

300 g of (R,S)-1-(4-methoxybenzyl)-octahydroisoquinoline are dissolved in 300 ml of isopropanol, and 67 ml of glacial acetic acid are added. Cooling down with stirring to 0° C. is followed by seeding with (R)-1-(4-methoxybenzyl)-octahydroisoquinolinium acetate. Slow stirring is continued at this temperature for 3 to 5 hours. The precipitated (R)-acetate is filtered off with suction and washed with tert.-butyl methyl ether. Yield: 88.8 g (48% of theory); melting point: 88°–89° C.; $[\alpha]_D^{20} = +116°$.

EXAMPLE 3

Sufficient racemic (R,S)-1-(4-methoxybenzyl)-octahydroisoquinolinium acetate is dissolved in isopropanol to form a 52.6% by weight (R,S)-1-(4-methoxybenzyl)-octahydroisoquinolinium acetate solution. The solution is seeded at 20° C. with about 1%, relative to the weight of the solution, of (S)-acetate and is stirred at 0° C. for 2 to 3 hours. The crystallized (S)-acetate is filtered off with suction and washed with tert.-butyl methyl ether.

By addition of fresh (R,S)-acetate to the mother liquor, the mother liquor concentration is readjusted to 52.6% by weight. Heating the solution to 50° C. for 10 minutes dissolves any crystal nuclei present. The solution is then seeded with about 1%, relative to the weight of the solution, of (R)-acetate and is stirred at 0° C. for 3 to 4 hours. The crystallized (R)-acetate is filtered off with suction and washed with tert.-butyl methyl ether.

The mother liquor is once more concentrated by addition of (R,S)-1-(4-methoxybenzyl)-octahydroisoquinolinium acetate to 52.6% by weight. 10 minutes of heating to 50° C. is followed by cooling down and seeding by addition of about 1%, relative to the weight of the solution, of (S)-acetate. The crystallized (S)-acetate is filtered off with suction and washed, and the mother liquor is as described above concentrated again by addition of racemate and seeded again with (R)-acetate.

The following table is a guide to the results obtained:

(97.3% of theory) of (S)-1-(4-methoxybenzyl)-octahydroisoquinoline.

The preceding examples can be repeated with similar success by substituting the generically or specifically described reactants and/or operating conditions of this invention for those used in the preceding examples.

From the foregoing description, one skilled in the art

| Separated enantiomer form | Addition of (RS)-MBI acetate | Seed material 0.90 g | Enantiomer isolation ||||||||| Mother liquors ||||
| | | | Salt yield || (S)-MBI acetate ||| (R)-MBI acetate ||| i-proH main mother liquor g | MTB wash conc. g | combined mother liquors contents ||
| | | | g excl. seed | % | g excl. seed | Optical purity % | Optical yield % | g excl. seed | Optical purity % | Optical yield % | | | (S)-acetate g | (R)-acetate g |
|---|---|---|---|---|---|---|---|---|---|---|---|---|---|---|
| (S) | 74,0 | (S) | 9,56 | 12,9 | 9,56 | 97,6 | 25,2 | | | | 119,1 | 6,48 | 27,57 | 36,87 |
| (R) | 9,56 | (R) | 22,24 | 30,1 | | | | 22,24 | 97,1 | 51,8 | 98,3 | 9,2 | 32,05 | 19,70 |
| (S) | 22,24 | (S) | 21,33 | 28,8 | 21,33 | 94,4 | 46,6 | | | | 96,1 | 10,7 | 22,40 | 30,26 |
| (R) | 21,33 | (R) | 19,91 | 26,9 | | | | 19,91 | 97,8 | 47,6 | 99,2 | 9,65 | 9,65 | 21,20 |
| (S) | 19,91 | (S) | 19,52 | 26,4 | 19,52 | 98,2 | 44,8 | | | | 97,35 | 10,1 | 23,45 | 31,03 |
| (R) | 19,52 | (R) | 17,58 | 23,8 | | | | 17,58 | 97,9 | 42,2 | 103,7 | 9,15 | 33,06 | 23,36 |
| (S) | 17,58 | (S) | 12,28 | 16,6 | 12,28 | 98,2 | 28,8 | | | | 111,8 | 7,6 | 29,64 | 31,89 |
| (R) | 12,28 | (R) | 11,9 | 16,1 | | | | 11,90 | 98,3 | 30,5 | 114,2 | 6,7 | 35,55 | 26,55 |
| (S) | 11,9 | (S) | 10,86 | 14,7 | 10,86 | 97,6 | 25,5 | | | | 115,0 | 6,95 | 30,73 | 32,40 |
| (R) | 10,86 | (R) | 11,46 | 15,5 | | | | 11,46 | 97,6 | 29,5 | 114,0 | 7,3 | 36,01 | 26,52 |
| (S) | 11,46 | (S) | 13,84 | 18,7 | 13,84 | 98,0 | 32,5 | | | | 108,8 | 7,6 | 28,00 | 32,15 |
| (R) | 13,84 | (R) | 10,7 | 14,5 | | | | 10,7 | 97,6 | 26,7 | 117,3 | 6,3 | 34,82 | 28,49 |
| (S) | 15,48 | (S) | 15,48 | 20,9 | | 98,4 | 37,4 | | | | | | 25,36 | 33,16 |
| (R) | 22,40 | (R) | 22,40 | 30,3 | | | | | 92,8 | 50,7 | | | 32,30 | 19,31 |

[MBI acetate = 1-(4-methoxybenzyl)-octahydroisoquinolinium acetate; i-PrOH = isopropanol; MTB = methyl tert.-butyl ether]

Concentration constantly 74.0 g of (RS)-MBI acetate (+0.9 g of seed material) in 141.5 g of i-PrOH solution. Replenishment of the separated-off enantiomers with fresh (RS)MBI acetate. 1.2% of seed material. Addition at 20° C. Previous denucleation 10 min/50° C. Crystallization times: (S) stage 2½ h/0° C.; (R) stage 3½ h/0° C.

EXAMPLE 4

A solution of 31.7 g of (S)-1-(4-methoxybenzyl)-octahydroisoquinolinium acetate in 250 ml of water is brought by addition of concentrated sodium hydroxide solution to pH 12. The free base is extracted twice with 150 ml of diethyl ether each time. Washing of the combined extracts with water, drying over sodium sulfate and removal of the solvent in vacuo leaves 25.0 g can easily ascertain the essential characteristics of this invention, and without departing from the spirit and scope thereof, can make various changes and modifications of the invention to adapt it to various usages and conditions.

What is claimed is:

1. (R,S)-1-(4-Methoxybenzyl)-1,2,3,4,5,6,7,8-octahydroisoquinolinium acetate, or the R-acetate or the S-acetate.

2. (R)-1-(4-Methoxybenzyl)-1,2,3,4,5,6,7,8-octahydroisoquinolinium acetate, a compound of claim 1.

3. (S)-1-(4-Methoxybenzyl)-1,2,3,4,5,6,7,8-octahydroisoquinolinium acetate, a compound of claim 1.

4. (R,S)-1-(4-Methoxybenzyl)-1,2,3,4,5,6,7,8-octahydroisoquinolinium acetate, racemic compound of claim 1.

* * * * *